(12) United States Patent
Yoshimura (10) Patent No.: US 10,092,273 B2
(45) Date of Patent: Oct. 9, 2018

(54) MEDICAL SYSTEM (71) Applicant: OLYMPUS CORPORATION, Tokyo (JP)

(72) Inventor: Takehiro Yoshimura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 51 days.

(21) Appl. No.: 14/944,712

(22) Filed: Nov. 18, 2015

(65) Prior Publication Data

US 2016/0074009 A1    Mar. 17, 2016

Related U.S. Application Data (63) Continuation of application No. PCT/JP2015/051094, filed on Jan. 16, 2015.

(30) Foreign Application Priority Data

Jan. 29, 2014    (JP) .................................. 2014-014683

(51) Int. Cl.
*G06F 3/048* (2013.01)
*A61B 8/00* (2006.01)
(Continued)

(52) U.S. Cl.
CPC ............... *A61B 8/468* (2013.01); *A61B 8/12* (2013.01); *A61B 8/461* (2013.01); *A61B 8/465* (2013.01);
(Continued)

(58) Field of Classification Search
CPC ..................................................... G06F 3/048
See application file for complete search history.

(56) References Cited

U.S. PATENT DOCUMENTS

2004/0054657 A1\* 3/2004 Takeyama ............... G06Q 10/10
2007/0250791 A1\* 10/2007 Halliday ................ G06Q 10/10
715/808

(Continued)

FOREIGN PATENT DOCUMENTS

EP          1821497 A1    8/2007
JP       2006-191279 A    7/2006

(Continued)

OTHER PUBLICATIONS

International Search Report dated Mar. 10, 2015 issued in PCT/JP2015/051094.

*Primary Examiner* — Xuyang Xia
(74) *Attorney, Agent, or Firm* — Scully, Scott, Murphy & Presser, P.C.

(57) ABSTRACT

A medical system includes an operation panel provided with an LCD touch panel and an ultrasound observation apparatus connected via a cable. When a comment receiving section of the operation panel receives comment information from a comment transmitting section of the ultrasound observation apparatus, an LCD image processing section changes a comment on the LCD touch panel according to the comment information, an operation control section sends out information about the change to an apparatus control section, and the ultrasound observation apparatus changes a comment display of a predetermined portion on a diagnosis monitor.

18 Claims, 8 Drawing Sheets

(51) Int. Cl.
*A61B 8/12* (2006.01)
*A61B 8/08* (2006.01)
*A61B 90/94* (2016.01)

(52) U.S. Cl.
CPC ............ *A61B 8/467* (2013.01); *A61B 8/5207* (2013.01); *A61B 8/54* (2013.01); *A61B 8/56* (2013.01); *A61B 90/94* (2016.02); *G06F 3/048* (2013.01)

(56) References Cited

U.S. PATENT DOCUMENTS

| | | | |
|---|---|---|---|
| 2008/0133996 A1* | 6/2008 | Naka | H04L 1/1671 714/748 |
| 2009/0085884 A1* | 4/2009 | Hibi | A61B 8/14 345/173 |
| 2010/0034442 A1* | 2/2010 | Minakuchi | G06F 19/3487 382/128 |

FOREIGN PATENT DOCUMENTS

| | | | |
|---|---|---|---|
| JP | 2006-325016 A | 11/2006 | |
| JP | 2007-330324 A | 12/2007 | |
| JP | 2009-106494 A | 5/2009 | |
| JP | WO 2012132840 A1 * | 10/2012 | ......... A61B 1/00009 |
| WO | WO 2006073038 A1 | 7/2006 | |
| WO | WO 2006/123462 A1 | 11/2006 | |

\* cited by examiner

MEDICAL SYSTEM

CROSS REFERENCE TO RELATED APPLICATION

This application is a continuation application of PCT/JP2015/051094 filed on Jan. 16, 2015 and claims benefit of Japanese Application No. 2014-014683 filed in Japan on Jan. 29, 2014, the entire contents of which are incorporated herein by this reference.

BACKGROUND OF THE INVENTION

1. Field of the Invention

The present invention relates to a medical system having an observation apparatus to which a medical apparatus for visualizing a shape, aspect or movement in a body to perform a predetermined examination can be connected.

2. Description of the Related Art

Various kinds of observation apparatuses to which a medical apparatus for visualizing a shape, aspect or movement in a body to perform a predetermined examination can be connected have been conventionally known. For example, an ultrasound observation apparatus to which an ultrasound probe, an electronic scanning type ultrasound endoscope or a mechanical scanning type ultrasound endoscope can be connected is known as a medical apparatus for performing an ultrasound examination using ultrasounds.

The ultrasound observation apparatus of this kind repeatedly transmits ultrasound pulses to living tissue from an ultrasound transducer of a connected ultrasound probe or an ultrasound endoscope, receives an echo signal of the ultrasound pulses reflected from the living tissue, generates information about an inside of a body as an ultrasound tomographic image, which is a visible image, and displays the ultrasound tomographic image on a display section such as a monitor.

Further, an ultrasound observation system has been also proposed recently in which a keyboard which carries out functions as an operation panel and is provided with an LCD (liquid crystal display) display section is connected to a body portion of the ultrasound observation apparatus of this kind to perform a predetermined operation.

On the other hand, in ultrasound endoscopic diagnosis, there has been a demand for a function of inputting, for example, names of surrounding organs or lymph nodes, to a diagnosis image displayed on a diagnosis monitor or the like connected to the ultrasound observation apparatus in order to identify a position of a region of interest.

In such an ultrasound observation system in which the keyboard as an operation panel is connected to the ultrasound operation apparatus as described above, a surgeon directly inputs a character string using character keys on the keyboard.

A technique has been conventionally known in which a list of a group of comments (a group of medical comments which are frequently inputted at time of diagnosis) registered with an ultrasound observation apparatus in advance is displayed on a diagnosis monitor (see FIG. 7), and an arbitrary comment on the diagnosis monitor is selected by selection means on an operation panel (keyboard), for example, a track ball (see Japanese Patent Application Laid-Open Publication No. 2007-330324).

Alternatively, a technique is also known in which a predetermined selection number is associated with each comment in the comment list displayed on the diagnosis monitor, and an arbitrary comment is selected by pressing the corresponding number key on the operation panel (keyboard).

Figure 8:
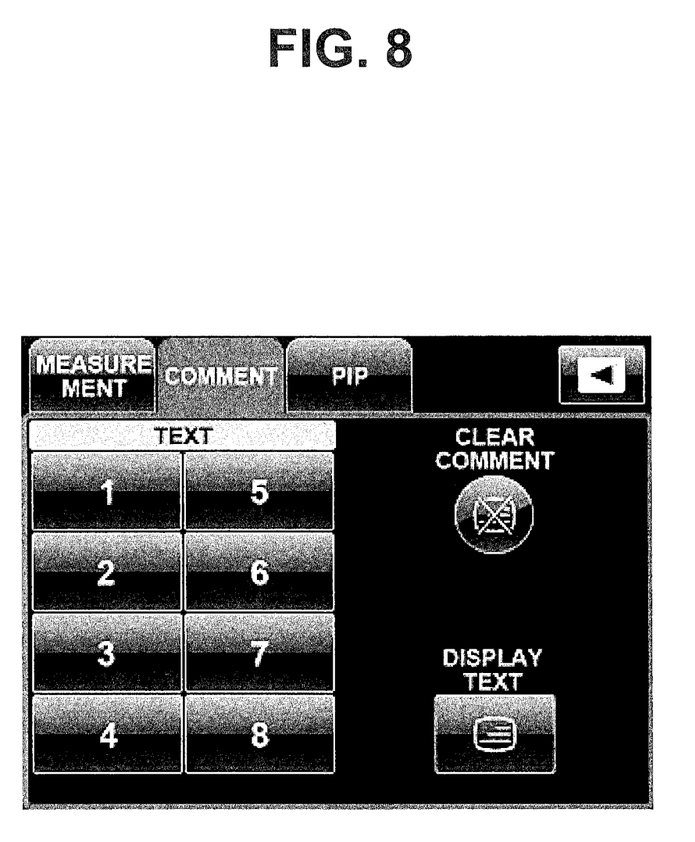
FIG. 8 is a diagram showing a display example of an LCD display section of an operation panel in the conventional ultrasound observation system.

Furthermore, a technique is also known in which the LCD display section of the operation panel is provided with a so-called touch panel function obtained by combining the LCD display section on the operation panel and a position input device, and a number button corresponding to the selection number associated with each comment in the comment list displayed on the diagnosis monitor is displayed so that an arbitrary comment is selected by touching the number button (see FIG. 8).

Further, in the techniques for selecting an arbitrary comment on the diagnosis monitor, a technique for changing a comment to be displayed, in response to switching to an observation mode (diagnosis region), an operation mode (for example, mechanical radial scanning, electronic radial scanning and electronic convex scanning) or the like so as to minimize the group of comments to be displayed on the diagnosis monitor, a technique enabling customization of displayed comments by a surgeon's preference, or the like is proposed.

SUMMARY OF THE INVENTION

A medical system of an aspect of the present invention is medical system capable of displaying desired character information on a subject image as a comment, the medical system including: an operation section provided with a touch panel; a first control section performing observation control of the subject image, the first control section being connected to the operation section via communication means; a storage section keeping comment group information corresponding to classifications of the comment in plurality; a first transmitting/receiving section reading out the comment group information from the storage section and transmitting/receiving the comment group information to/from the operation section; a second transmitting/receiving section transmitting/receiving the comment group information to/from the first transmitting/receiving section, the second transmitting/receiving section being provided in the operation section; a touch panel image processing section displaying a corresponding comment on the touch panel according to the comment group information received by the second transmitting/receiving section, the touch panel image processing section being provided in the operation section; an image processing section reading out, when a desired comment on the touch panel is selected in a state that the comment in plurality are displayed on the touch panel by the touch panel image processing section, the comment on the touch panel received by the first transmitting/receiving section from the storage section, and displaying the corresponding comment on the subject image; a second control section controlling the first and second transmitting/receiving sections to read out the comment group information and transmit the comment group information to the first control section, the second control section being provided in the operation section; and a comment transmission/reception instructing section controlling transmission/reception of the comment group information according to a state of processing load of the first or second control section, the comment transmission/reception instructing section being connected to the first and second control sections.

DETAILED DESCRIPTION OF THE PREFERRED EMBODIMENTS

Embodiments of the present invention will be described below with reference to drawings.

First Embodiment

Figure 1:
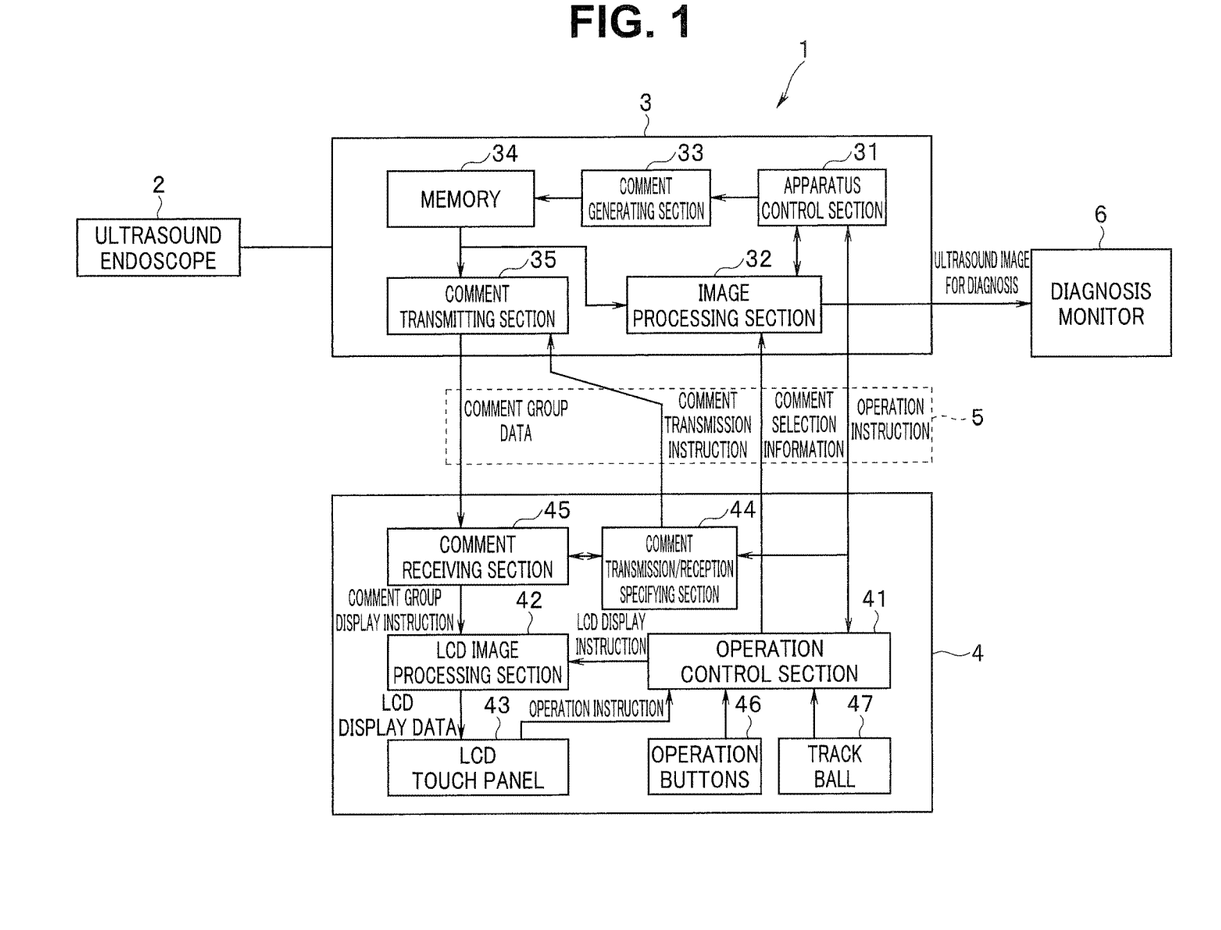
FIG. 1 is a diagram showing a configuration of an ultrasound observation system of a first embodiment of the present invention.

FIG. 1 is a diagram showing a configuration of an ultrasound observation system 1 of a first embodiment of the present invention.

As shown in FIG. 1, the ultrasound observation system 1 of the present invention is characterized in transmitting an ultrasound to a subject, receiving the ultrasound reflected by the subject and generating an image on a basis of an ultrasound signal obtained from the received ultrasound.

That is, the ultrasound observation system 1 is provided with: for example, an electronic scanning type ultrasound endoscope 2 having an ultrasound transducer which transmits an ultrasound to a subject, receives the ultrasound reflected by the subject and generates an ultrasound signal from the received ultrasound; an ultrasound observation apparatus 3 provided with image generating means for generating an ultrasound image on a basis of the ultrasound signal obtained from the electronic scanning type ultrasound endoscope 2; an operation panel 4 connected to a body portion of the ultrasound observation apparatus 3 to give a predetermined instruction; a cable 5 as communication means for performing transmission of predetermined data between the ultrasound observation apparatus 3 and the operation panel 4; and a diagnosis monitor 6 which displays the ultrasound image generated by the ultrasound observation apparatus 3 to provide the ultrasound image for diagnosis by a surgeon.

Figure 2:
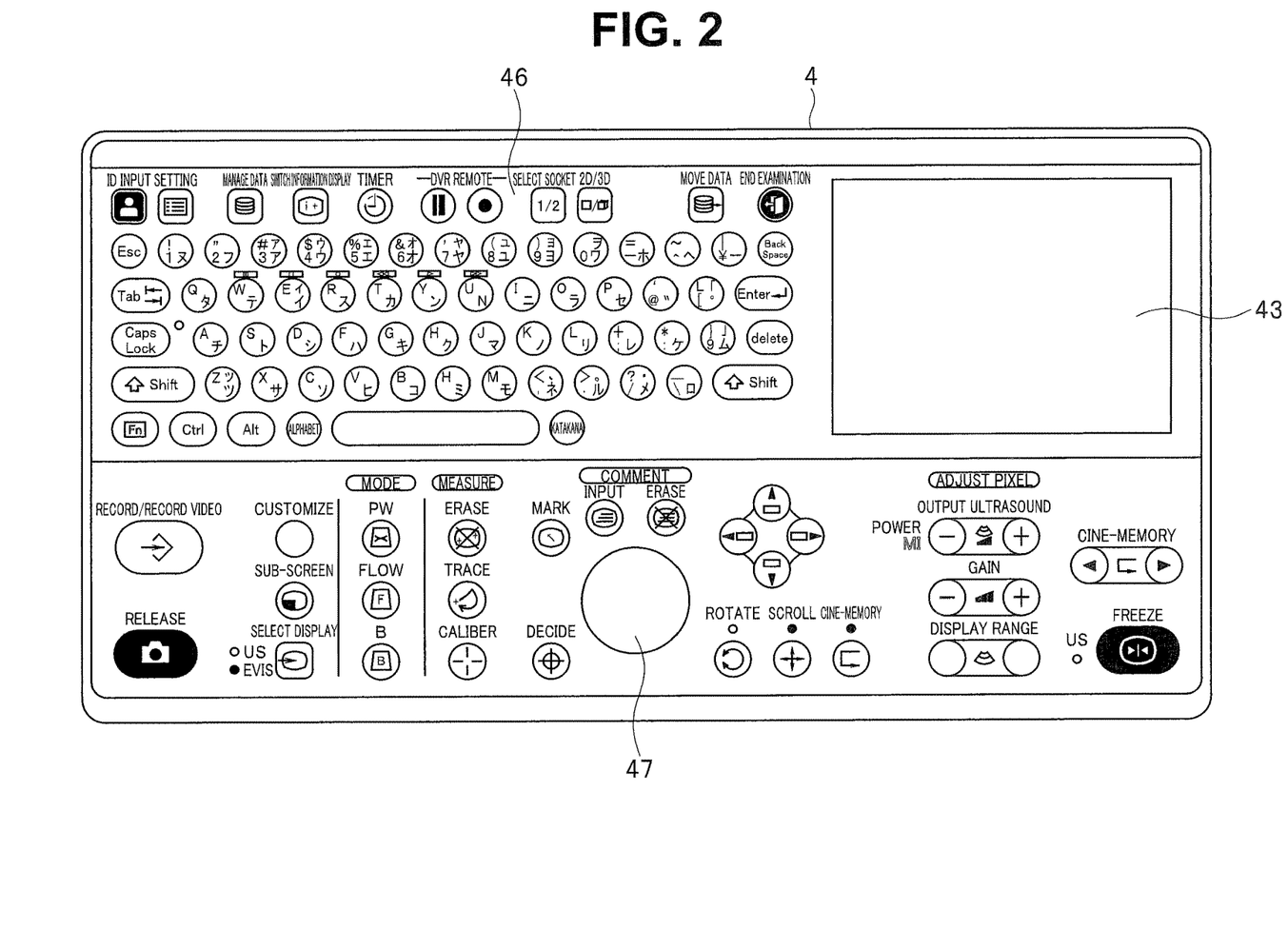
FIG. 2 is a front view showing an operation panel in the ultrasound observation system of the first embodiment.

FIG. 2 is a front view showing the operation panel 4 in the ultrasound observation system 1 of the first embodiment.

As shown in FIG. 2, the operation panel 4 is a keyboard connected to the body portion of the ultrasound observation apparatus 3 and is provided with operation buttons 46 configured with a mechanical tact switch, a membrane switch and the like, a track ball 47 and an LCD touch panel 43.

Here, the LCD touch panel 43 is provided with a so-called touch panel function obtained by combining an LCD (liquid crystal display) display section and a position input device, and positions of coordinates on the panel are determined in advance.

For example, by touching an arbitrary position on the touch panel, an operator can recognize a coordinate position of the touched position on the panel.

Further, on a rear face of the operation panel 4 (on an upper side of the keyboard section in FIG. 2), a connector for connection with the ultrasound observation apparatus 3 or other peripheral apparatuses (another endoscopic diagnostic apparatus and the like) is arranged.

Returning to FIG. 1, the operation panel 4 is connected to the ultrasound observation apparatus 3 via the cable 5 and is provided with operation means (the operation buttons 46, the track ball 47 and the LCD touch panel 43), control means (an operation control section 41 and an LCD image processing section 42), a comment transmission/reception instructing section 44 and a comment receiving section 45.

The operation buttons 46, the track ball 47 and the LCD touch panel 43 are connected to the operation control section 41 so as to send out an operation instruction corresponding to an operation by the surgeon to the operation control section 41.

Further, the operation control section 41 is connected to an apparatus control section 31 of the ultrasound observation apparatus 3 so as to send out a predetermined operation instruction to the ultrasound observation apparatus 3.

Furthermore, the operation control section 41 is also connected to the LCD image processing section 42 and sends out a predetermined LCD display instruction to the LCD image processing section 42.

The LCD image processing section 42 is connected to the LCD touch panel 43 and sends out predetermined LCD display data to the LCD touch panel 43 under control of the operation control section 41.

The comment transmission/reception instructing section 44 is connected to a comment transmitting section 35 and the operation control section 41 of the ultrasound observation apparatus 3. The comment transmission/reception instructing section 44 monitors a state of a processing load of the operation control section 41 and gives an instruction regarding a sending-out timing, an amount of data and a transmission/reception method for comment group data to be sent out from the comment transmitting section 35 of the ultrasound observation apparatus 3, to the comment transmitting section 35.

The comment receiving section 45 is connected to the ultrasound observation apparatus 3 and the LCD image processing section 42, and sends out a comment group display instruction to the LCD image processing section 42 on a basis of the comment group data sent from the comment transmitting section 35 of the ultrasound observation apparatus 3.

Further, the comment receiving section 45 is also connected to the comment transmission/reception instructing section 44, monitors whether communication of the comment group data from the comment transmitting section 35 of the ultrasound observation apparatus 3 is successful or not, and, if the communication is failed, notifies the comment transmission/reception instructing section 44 of information about at which position the failure occurred.

On the other hand, the ultrasound observation apparatus 3 is provided with: the apparatus control section 31 which controls each circuit in the apparatus body, an image processing section 32 which generates a predetermined ultrasound image on a basis of an ultrasound signal from the electronic scanning type ultrasound endoscope 2, and comment processing means for registering and changing a comment (a comment generating section 33, a memory 34 and a comment transmitting section 35) as shown in FIG. 1.

The apparatus control section 31 is connected to the operation panel 4 and the image processing section 32, and controls various settings in the apparatus body as well as sending out various setting instructions for generation of an ultrasound image to the image processing section 32, according to operation instructions from the operation control section 41 of the operation panel 4.

Further, the apparatus control section 31 is also connected to the comment generating section 33 and sends out instructions to generate and update a comment, to the comment generating section 33.

The comment generating section 33 is connected to the memory 34 so as to write a generated comment group to the memory 34.

At this time, the comment generating section 33 writes the comment group information into the memory 34 in association with information about a coordinate position on the LCD touch panel 43 corresponding to each comment.

The comment transmitting section 35 is connected to the operation panel 4 and the memory 34, acquires comment group data from the memory 34 according to a comment transmission instruction from the comment transmission/reception instructing section 44 of the operation panel 4, and sends out an arbitrary amount of the comment group data to the comment receiving section 45 of the operation panel 4 at arbitrary timing and in an arbitrary transmission/reception method.

The image processing section 32 is connected to the apparatus control section 31 and the diagnosis monitor 6, and the image processing section 32 generates an ultrasound image on a basis of an ultrasound signal obtained from the electronic scanning type ultrasound endoscope 2 according to an instruction of the apparatus control section 31 and sends out the ultrasound image to the diagnosis monitor 6.

Further, the image processing section 32 is also connected to the memory 34, and, if a comment input operation instruction is given from the apparatus control section 31, performs a process for acquiring comment group data from the memory 34 and adding the comment group data to the ultrasound image.

After that, if receiving comment selection information from the operation panel 4, the image processing section 32 also performs a process for inputting the selected comment to the ultrasound image. Note that, in this case, the comment selection information may be received directly from the operation panel 4 or via the apparatus control section 31.

Figure 7:
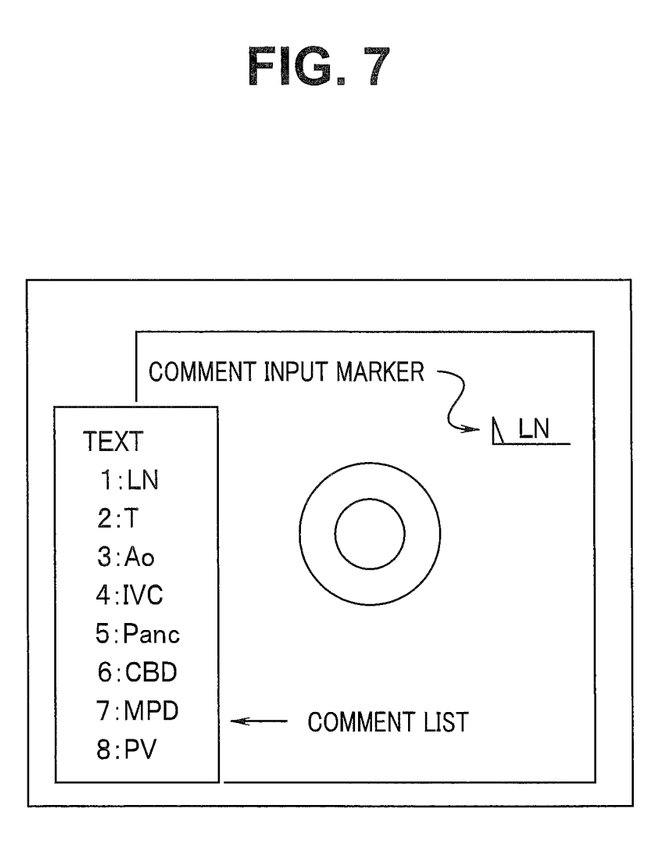
FIG. 7 is a diagram showing a display example of a diagnosis monitor in a conventional ultrasound observation system.

As described above, in a conventional ultrasound observation system, only numbers are displayed on buttons of a comment input screen (LCD touch panel screen) of an operation panel 4 as shown in FIG. 8, and it is common to, at time of inputting a comment, perform a keyboard button operation while confirming a comment list added to an ultrasound image displayed on a diagnosis monitor as shown in FIG. 7.

Figure 3:
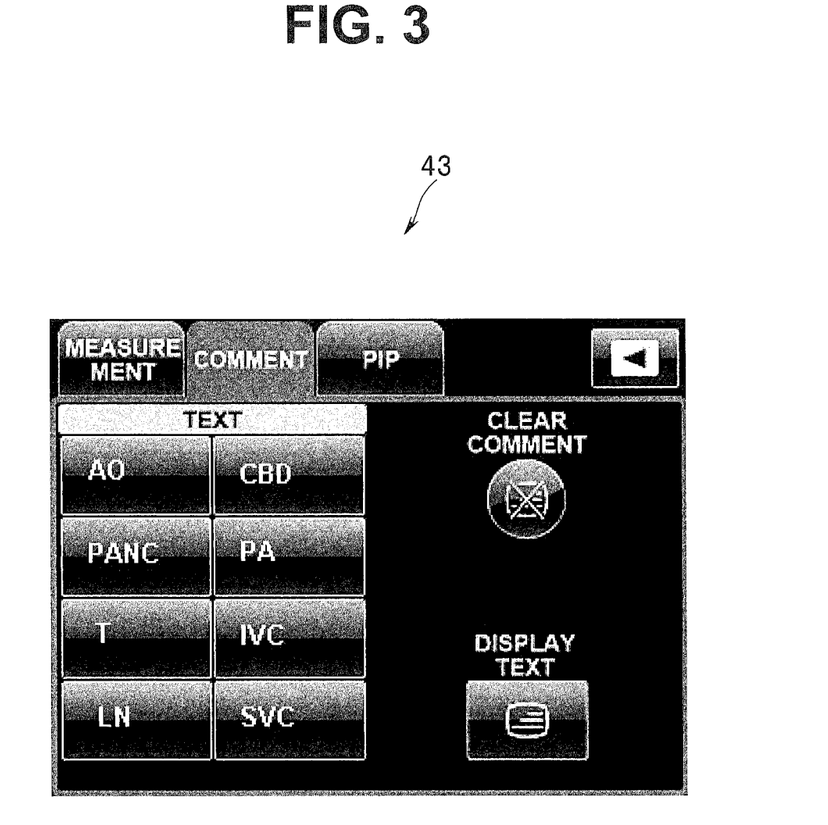
FIG. 3 is a diagram showing a display example of an LCD display section of the operation panel in the ultrasound observation system of the first embodiment.

In comparison, in the ultrasound observation system 1 of the present embodiment, comments specified from the ultrasound observation apparatus 3, for example, "AO", "PANC", "T", "LN", "CBD", "PA", "IVC" and "SVC" are displayed in the shape of buttons on a comment input screen of the operation panel 4, that is, the LCD touch panel 43 as shown in FIG. 3.

Figure 4:
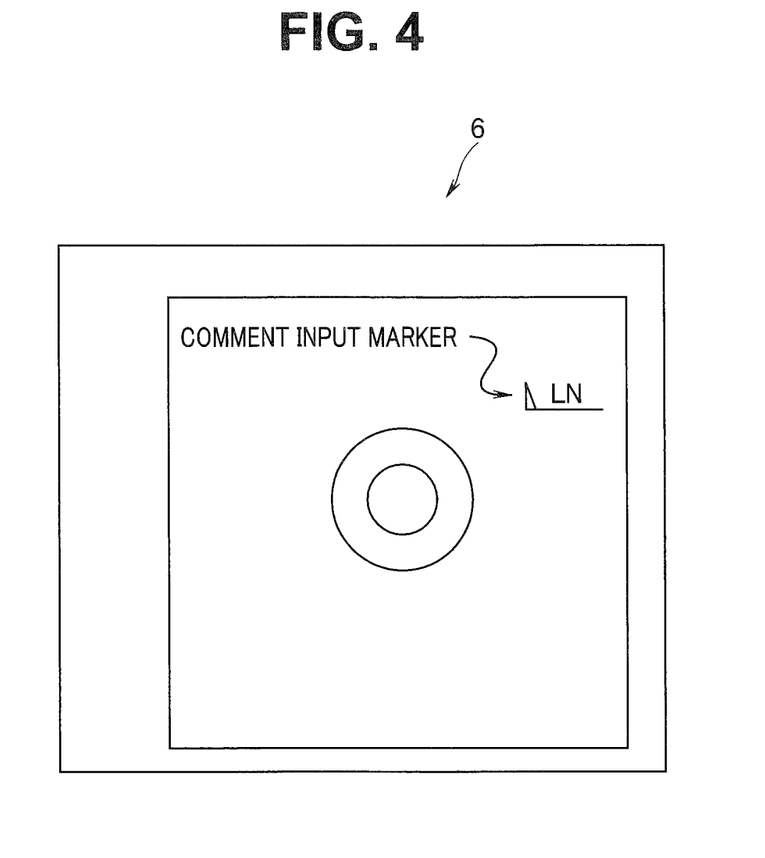
FIG. 4 is a diagram showing a display example of a diagnosis monitor in the ultrasound observation system of the first embodiment.

As shown in FIG. 3, it is possible to confirm comments registered with the ultrasound observation apparatus 3, on the LCD touch panel 43 of the operation panel 4 in the present embodiment; and it becomes possible to, by pressing down a button portion (touching the touch panel) to which the comment is given, input a selected comment at an arbitrary position on the diagnosis monitor 6 as shown in FIG. 4.

That is, in the ultrasound observation system 1 of the first embodiment, when the comment receiving section 45 of the operation panel 4 receives predetermined comment information from the comment transmitting section 35 of the ultrasound observation apparatus 3, the LCD image processing section 42 of the operation panel 4 changes a comment on the button on the LCD touch panel 43 according to the comment information under control of the operation control section 41.

Furthermore, the operation control section 41 sends out information about the change on the LCD touch panel 43 to the apparatus control section 31 of the ultrasound observation apparatus 3.

In response to this, the apparatus control section 31 controls the image processing section 32 to change a comment display on a predetermined portion on the diagnosis monitor 6.

Next, a communication sequence between the ultrasound observation apparatus 3 and the operation panel 4 in the ultrasound observation system 1 of the present embodiment will be described.

Figure 5:
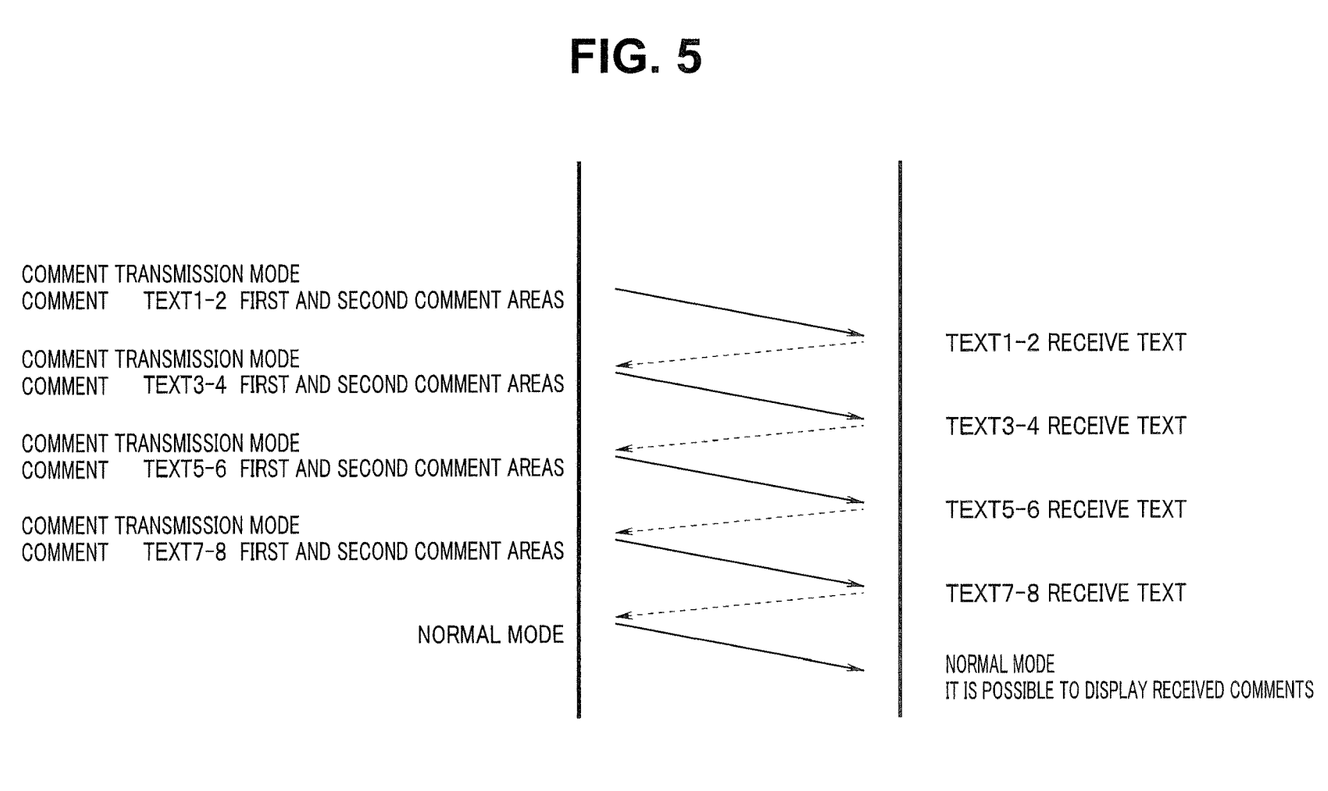
FIG. 5 is a diagram showing a communication sequence between an ultrasound observation apparatus and the operation panel in the ultrasound observation system of the first embodiment.

FIG. 5 is a diagram showing the communication sequence between the ultrasound observation apparatus 3 and the operation panel 4 in the ultrasound observation system 1 of the first embodiment.

In the ultrasound observation system 1 of the present embodiment, eight comments can be registered and edited for each observation mode (preset for each diagnosis region or for each scope) in the ultrasound observation apparatus 3. The maximum number of characters for each button is six.

That is, the maximum number of characters received by the operation panel 4 side is: 8 [buttons/modes]×6[characters/buttons]=48 characters.

In the present embodiment, the eight comments described above are set as TEXT 1 to 8, respectively. Regarding two comment groups as one set, transmission/reception is performed up to four times by performing handshaking for each set.

At that time, that is, during a comment transmission mode, the apparatus control section 31 and the operation control section 41 are blocked so that communication other than communication for the comments does not occur from the apparatus control section 31 or the operation control section 41. Further, if communication fails while it is being performed, only a failed comment group is transmitted/received again.

Further, at time of activation, all the comments TEXT 1 to 8 of a current observation mode are transmitted to the operation panel 4.

Furthermore, when the observation mode is switched, all the comments TEXT 1 to 8 of a newly switched observation mode are transmitted to the operation panel 4.

When a comment is modified, only the changed comment or comment group is transmitted to the operation panel 4.

Note that the number of transferred character bits may be restricted to be smaller by limiting displayed characters to alphanumeric characters.

As described above, in the ultrasound observation system 1 of the first embodiment, when the comment receiving section 45 of the operation panel 4 receives predetermined comment information from the comment transmitting section 35 of the ultrasound observation apparatus 3, the LCD image processing section 42 of the operation panel 4 changes a comment on the button on the LCD touch panel 43 according to the comment information under control of the operation control section 41.

Furthermore, the operation control section 41 sends out information about the change on the LCD touch panel 43 to the apparatus control section 31 of the ultrasound observation apparatus 3.

In response to this, the apparatus control section 31 controls the image processing section 32 to change a comment display on a predetermined portion on the diagnosis monitor 6.

As described above, according to the ultrasound observation system 1 of the present first embodiment, comments registered with the ultrasound observation apparatus 3 can be confirmed on the operation panel 4 (the LCD touch panel 43), and, therefore, it is possible to perform input more intuitively and simply.

Further, according to the ultrasound observation system 1 of the present first embodiment, it is not necessary to display a comment list registered with the ultrasound observation apparatus 3 on an ultrasound image (a diagnosis image) on the diagnosis monitor 6, and, therefore, it becomes easy to perform image diagnosis.

In other words, it is possible to appropriately display desired character information on a diagnosis image displayed on the diagnosis monitor without decreasing efficiency of image diagnosis.

Furthermore, according to the ultrasound observation system 1 of the present first embodiment, it is possible to adopt a cable with a small diameter as a cable for connecting the ultrasound observation apparatus 3 and the operation panel 4 without requiring a dedicated video cable (for example, an RGB cable with a diameter of about 15 mm) for displaying comments, and, therefore, it becomes easy to handle the operation panel 4.

Furthermore, according to the ultrasound observation system 1 of the present first embodiment, it is possible to prevent delay of an operation signal from the operation panel 4 by limiting a timing of transmitting/receiving a comment.

Furthermore, according to the ultrasound observation system 1 of the present first embodiment, by limiting transmission/reception only to transmission/reception of change in a comment, a transmission/reception time period is shortened, and influence on operability is reduced more.

Furthermore, according to the ultrasound observation system 1 of the present first embodiment, by performing transmission/reception of comments in a plurality of times, a length of data communicated each time can be suppressed, and a time period required for recovery at time of a communication error is shortened.

Furthermore, according to the ultrasound observation system 1 of the present first embodiment, correspondence between information in the ultrasound observation apparatus 3 and information on the operation panel 4 is enhanced by performing handshaking of a comment transmission/reception method.

Second Embodiment

Figure 6:
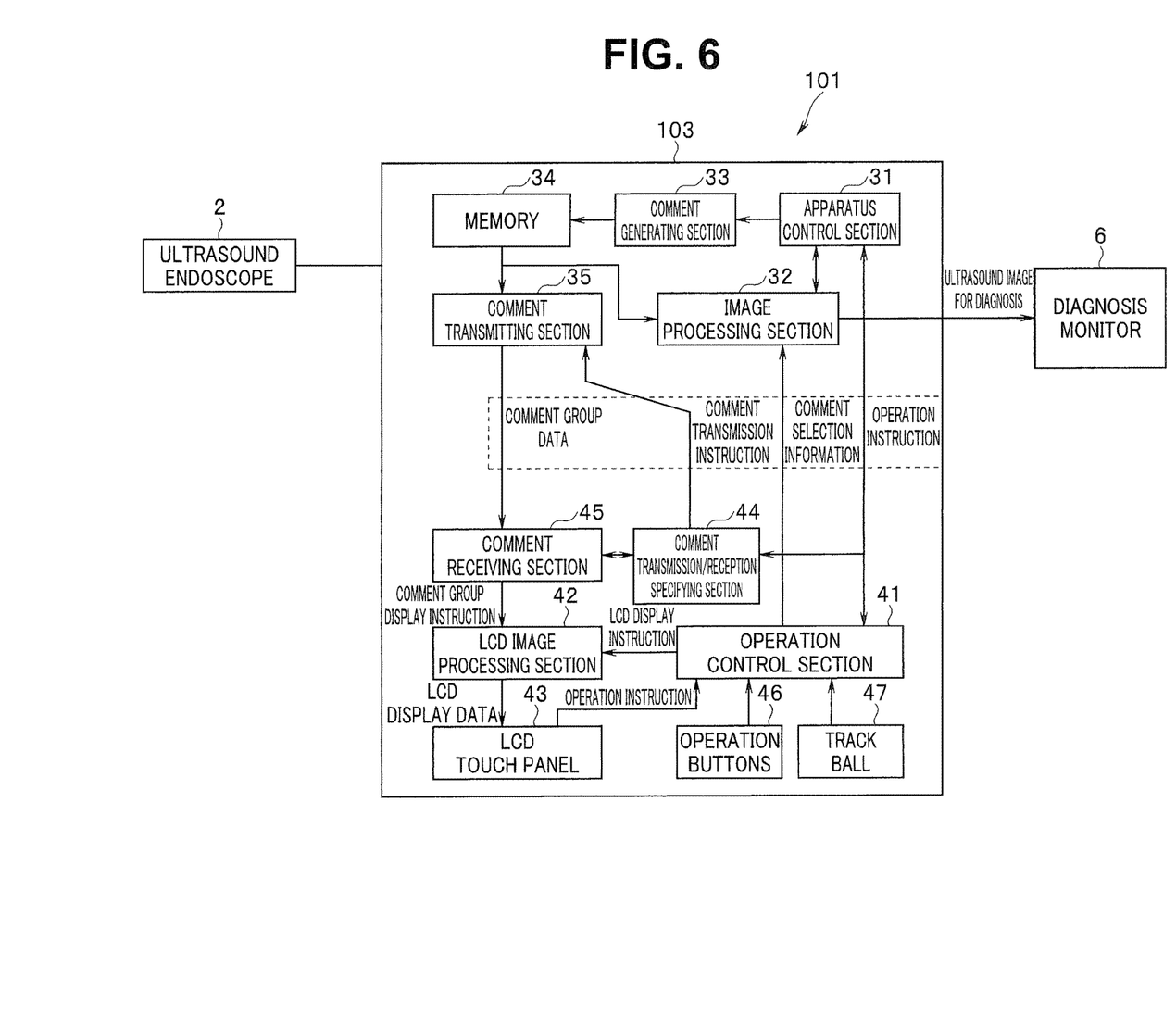
FIG. 6 is a diagram showing a configuration of an ultrasound observation system of a second embodiment of the present invention.

FIG. 6 is a diagram showing a configuration of an ultrasound observation system 101 of a second embodiment of the present invention.

As described above, the ultrasound observation system 1 of the first embodiment of the present invention is provided with the ultrasound observation apparatus 3 and the operation panel 4 which is connected to the ultrasound observation apparatus 3 via the cable 5 and is a body separate from the ultrasound observation apparatus 3.

The memory 34, the comment generating section 33 and the like are provided on the ultrasound observation apparatus 3 side, and the LCD touch panel 43 and the like are provided on the operation panel 4 side.

In comparison, the ultrasound observation system 101 of the present second embodiment is characterized in being configured by integrating components of the ultrasound observation apparatus 3 and components of the operation panel 4 in the first embodiment. That is, in the ultrasound observation system 101 in the second embodiment, an ultrasound observation apparatus 103 is integrally provided with functions of the operation panel 4 including the LCD touch panel 43.

Furthermore, the cable 5 connecting the ultrasound observation apparatus 3 and the operation panel 4 in the first embodiment is replaced with wiring inside the ultrasound observation apparatus 103.

Note that, since other configuration characteristics are similar to those of the first embodiment, detailed description of the characteristics will be omitted here.

In the second embodiment also, comment group data and the like are transmitted/received by a communication sequence as shown in FIG. 5 similarly to the first embodiment described above so that effects other than the effects of the cable 5 can be obtained.

That is, by the ultrasound observation system 101 of the second embodiment also, effects similar to those of the first embodiment can be obtained, such as being able to perform input more intuitively and simply since it is possible to confirm registered comments on the LCD touch panel 43, and being able to perform image diagnosis easily since it is not necessary to display a registered comment list on an ultrasound image (a diagnosis image) on the diagnosis monitor 6.

Further, though the memory 34 and the comment generating section 33 are provided on the ultrasound observation apparatus 3 side in the first embodiment described above, the configuration is not limited to this. For example, the memory 34 and the comment generating section 33 may be provided on the electronic scanning type ultrasound endoscope 2 side or the operation panel 4 side within the range not departing from the technical idea of the present invention, the electronic scanning type ultrasound endoscope 2 and the ultrasound observation apparatus 3 being connected to the ultrasound observation apparatus 3.

Furthermore, though an ultrasound observation system is given as an example of an embodiment of a medical system of the present invention in each embodiment described above, the technical idea of the present invention can be applied to other medical systems capable of displaying desired character information on a subject image as a comment, for example, diagnosis systems such as CT (computed tomography) and MRI (magnetic resonance imaging) systems for obtaining a tomographic image of a subject.

Note that the present invention is not limited to the embodiments described above as they are, and it is possible to transform and embody components within a range not departing from the spirit of the invention at a stage of implementation. Further, it is possible to form various aspects of the invention by appropriately combining a plurality of components disclosed in the above embodiments. For example, some components may be deleted from all the components shown in the embodiments. Furthermore, components of the different embodiments may be appropriately combined.

As described above, it goes without saying that various modifications or applications are possible within the range not departing from the spirit of the invention.

What is claimed is:

1. A medical system of displaying, on a monitor, desired character information on a subject image as a comment, the medical system comprising:
    an operation section provided with a touch panel which is a body separate from the monitor and formed by combining a display and a position input device;
    a first controller configured to perform observation control of the subject image, the first controller being connected to the operation section;
    a memory for storing comment group information corresponding to classifications of the comment in plurality;
    the first controller being configured to read out the comment group information from the memory and transmit/receive the comment group information to/from the operation section; and
    a second controller being provided in the operation section and connected to the first controller, the second controller being configured to transmit/receive the comment group information to/from the first controller to generate a plurality of button images in which comments are displayed according to the comment group information received by the second controller, and display the plurality of button images side by side on the touch panel,
    wherein the first controller being further configured to read out the comment on the touch panel received by the first controller from the memory, and display the comment on the subject image on the monitor,
    wherein the second controller being further configured to read out the comment group information and transmit the comment group information to the first controller and control transmission/reception of the comment group information according to a state of processing load of the first or second controller,
    wherein the comment is character information that includes at least alphanumeric characters or symbols,
    wherein the character information of the comment displayed on the subject image is equivalent to the character information of the comment selected from the plurality of button images, and
    wherein the second controller controls the display of the touch panel to display the plurality of button images including the character information, and when a user's instruction is inputted through the position input device of the touch panel by touching one of the plurality of button images to which the comment is given, the first controller controls the monitor to display the character information on the subject image in response to the user's input instruction.

2. The medical system according to claim 1,
    wherein the comment group information stored in the memory includes information about a position on the touch panel corresponding to each of the comments;
    the second controller being further configured to display a comment corresponding to the corresponding position on the touch panel according to the information about the position on the touch panel of the comment group information; and
    the first controller being further configured to read out the corresponding comment from the memory according to the information about the position on the touch panel of the comment group information received by the first controller, and display the corresponding comment on the subject image.

3. The medical system according to claim 2,
    wherein the medical system according to claim 2 is an ultrasound observation system capable of displaying desired character information on an ultrasound image of a subject as a comment;
    the first controller being further configured to:
        perform ultrasound observation control of the subject image
        read out, when a desired comment on the touch panel is selected in the state that the comment in plurality are displayed on the touch panel, a corresponding comment according to information about a position on the touch panel received by the first controller from the memory, and
        display the corresponding comment on the ultrasound image of the subject.

4. The medical system according to claim 3, comprising an ultrasound observation apparatus providing predetermined image processing for the subject image and causing the subject image to be displayed on an external monitor,
    wherein the operation section is configured separately from an ultrasound observation apparatus body portion of the ultrasound observation apparatus;
    the first controller and the memory are provided in the ultrasound observation apparatus body portion; and
    the first controller in the ultrasound observation apparatus body portion and the second controller in the operation section are connected via a cable.

5. The medical system according to claim 4,
    wherein the ultrasound observation apparatus body portion further comprises:
    an input device inputting an arbitrary comment as a comment of the comment group information; and
    the first controller is configured to cause a comment changed by the input device to be stored into the memory.

6. The medical system according to claim 5,
    wherein the second controller is further configured to give an instruction regarding transmission of the comment group information stored in the memory at at least one timing among time of activating the ultrasound observation apparatus, time of connecting the operation section and the ultrasound observation apparatus body portion, time of changing an ultrasound observation mode, time of changing a surgeon and time of updating the comment group information.

7. The medical system according to claim 6,
    wherein the second controller is further configured to transmit/receive all of the comment group information at the time of activating the ultrasound observation apparatus, at the time of connecting the operation section and the ultrasound observation apparatus body portion, at the time of changing the ultrasound observation mode or at the time of changing the surgeon, transmit/receive only an updated part of the comment group information at the time of updating the comment group information, and transmit/receive only a part of the comment group information for which transmission/reception is failed at the time of transmission/reception by the first or second controllers being failed.

8. The medical system according to claim 3,
    wherein the second controller is further configured to judge whether transmission/reception of the comment group information is successful or not, and give an instruction regarding retransmission, a retransmission timing, or an amount of information to be retransmitted, to the first controller.

9. The medical system according to claim 8, wherein the first and second controllers use a sequence for mutual confirmation and notify whether mutual communication is successful or not and the comment group information for which mutual communication is failed.

10. The medical system according to claim 8, wherein the first and second controllers divide the comment group information into one or more blocks to transmit/receive the comment group information, and transmit/receive all of the comment group information or selectively transmit/receive each of the blocks according to an instruction from the second controller.

11. The medical system according to claim 10, wherein the second controller is further configured to judge whether transmission/reception of the comment group information is successful or not for each of the blocks, and perform again transmission/reception of only a block for which transmission/reception is failed.

12. The medical system according to claim 1, wherein the second controller is further configured to monitor a state of information processing by an ultrasound observation operation in the ultrasound observation apparatus body portion, and control transmission/reception of the comment group information according to an information processing load of the ultrasound observation apparatus body portion.

13. The medical system according to claim 12, wherein, in order to prioritize information processing due to the ultrasound observation operation in the ultrasound observation apparatus body portion, the second controller is further configured to inhibit transmission/reception of the comment group information when the information processing load of the ultrasound observation apparatus body portion is high and permit transmission/reception of the comment group information when the information processing load is low.

14. The medical system according to claim 1, wherein the comment group information has a plurality of information sets, and one desired information set is selected according to an observation mode, an observation target, a patient or a surgeon.

15. The medical system according to claim 14, wherein the one desired information set in the comment group information is manually or automatically selected according to the observation mode, the observation target, the patient or the surgeon.

16. The medical system according to claim 1, wherein the character information is TEXT data.

17. The medical system according to claim 1, wherein the comment is a medical comment.

18. The medical system according to claim 1, wherein the first controller includes an image processing section, and
the image processing section is connected to the memory, and the image processing section acquires the comment group information from the memory in response to an instruction of the operation section, to add the comment group information to the subject image.

* * * * *